(12) United States Patent
Kasodekar et al.

(10) Patent No.: US 9,173,716 B2
(45) Date of Patent: Nov. 3, 2015

(54) COMPUTER-AIDED PLANNING WITH DUAL ALPHA ANGLES IN FEMORAL ACETABULAR IMPINGEMENT SURGERY

(75) Inventors: Snehal Kasodekar, Plantation, FL (US); Hyosig Kang, Weston, FL (US); Alon Mozes, Miami Beach, FL (US)

(73) Assignee: MAKO SURGICAL CORPORATION, Fort Lauderdale, FL (US)

( * ) Notice: Subject to any disclaimer, the term of this patent is extended or adjusted under 35 U.S.C. 154(b) by 461 days.

(21) Appl. No.: 13/291,654

(22) Filed: Nov. 8, 2011

(65) Prior Publication Data

US 2013/0114866 A1 May 9, 2013

(51) Int. Cl.
| | |
|---|---|
| *A61B 5/00* | (2006.01) |
| *A61B 19/00* | (2006.01) |
| *A61B 5/107* | (2006.01) |
| *G06T 7/00* | (2006.01) |
| *G06T 7/60* | (2006.01) |

(52) U.S. Cl.
CPC ............... *A61B 19/50* (2013.01); *A61B 5/1071* (2013.01); *A61B 5/4504* (2013.01); *A61B 5/4571* (2013.01); *G06T 7/0085* (2013.01); *G06T 7/602* (2013.01); *A61B 2019/504* (2013.01); *A61B 2019/505* (2013.01); *G06T 2207/30008* (2013.01)

(58) Field of Classification Search
None
See application file for complete search history.

(56) References Cited

U.S. PATENT DOCUMENTS

| | | |
|---|---|---|
| 5,871,018 A | 2/1999 | Delp et al. |
| 6,205,411 B1 | 3/2001 | DiGioia, III et al. |
| 7,427,200 B2 | 9/2008 | Noble et al. |
| 7,699,793 B2 | 4/2010 | Götte et al. |
| 7,769,429 B2 | 8/2010 | Hu |
| 7,813,784 B2 | 10/2010 | Marquart et al. |
| 7,815,644 B2 | 10/2010 | Masini |
| 2006/0165268 A1 | 7/2006 | Kaus et al. |
| 2007/0038059 A1 | 2/2007 | Sheffer et al. |
| 2007/0198022 A1 | 8/2007 | Lang et al. |
| 2007/0249967 A1 | 10/2007 | Buly et al. |
| 2008/0075348 A1 | 3/2008 | Rappaport et al. |
| 2008/0139922 A1 | 6/2008 | Pelletier et al. |
| 2008/0183104 A1 | 7/2008 | Tuma et al. |
| 2008/0312663 A1 | 12/2008 | Haimerl et al. |
| 2009/0209884 A1 | 8/2009 | Van Vorhis et al. |

(Continued)

OTHER PUBLICATIONS

Mamisch; *Range of Motion after CT based simulation of Intertrochanteric Corrective Osteotomy in cases of Slipped Capital Femoral Epiphysis (SCFE: Comparison of uniplanar flexion osteotomy and multi-planar fexion-, valgistation and rotational osteotomy*; article; Jun. 29, 2009; pp. 336-340; J Pediatr Orthop.

(Continued)

*Primary Examiner* — Jon Chang
(74) *Attorney, Agent, or Firm* — Miller, Matthias & Hull LLP

(57) ABSTRACT

A method for determining a resection volume of a pathologic femur having a femoral head and a femoral neck is provided. The method may determine a first point of a desired contour based on a pathologic alpha angle of the pathologic femur, determine a second point of the desired contour based on a desired alpha angle of the pathologic femur, determine a third point of the desired contour on the femoral neck of the pathologic femur, and generate a resection volume of the pathologic femur based on the first, second and third points of the desired contour.

20 Claims, 16 Drawing Sheets

(56) References Cited

U.S. PATENT DOCUMENTS

| | | |
|---|---|---|
| 2009/0285465 A1 | 11/2009 | Haimerl et al. |
| 2010/0086181 A1 | 4/2010 | Zug et al. |
| 2011/0015639 A1 | 1/2011 | Metzger et al. |
| 2011/0071802 A1 | 3/2011 | Bojarski et al. |
| 2011/0257518 A1* | 10/2011 | Buly et al. .................... 600/427 |
| 2013/0085723 A1* | 4/2013 | Chabanas et al. ................. 703/1 |
| 2013/0089253 A1* | 4/2013 | Chabanas et al. ............. 382/131 |

OTHER PUBLICATIONS

Kubiak-Langer; *Range of Motion in Anterior Femoroacetabular Impingement*; article; May 2007; pp. 117-124; vol. 458; Clinical Orthopaedics & Related Research.

Richolt; *Impingement Simulation of the Hip in SCFE Using 3D Models*; article;1999; pp. 144-151; Comput. Aided. Surg., (Abstract Only).

* cited by examiner

COMPUTER-AIDED PLANNING WITH DUAL ALPHA ANGLES IN FEMORAL ACETABULAR IMPINGEMENT SURGERY

TECHNICAL FIELD

The present disclosure relates generally to surgical planning, and more particularly, to computer-aided systems and methods for planning orthopedic surgery.

BACKGROUND

Resectional surgery is a commonly applied practice in the field of orthopedics. Among other things, resectional surgery can be used to surgically treat orthopedic deformities or overgrowths in bone structures which may otherwise cause substantial discomfort and limit the range of motion in the affected region. A common complication involving such a deformity includes femoral acetabular impingement (FAI). An FAI is a condition in which movement of the hip joint is limited by an impingement between the acetabulum, or socket, of the pelvis and the head of the femur, or femoral head, pivotally attached thereto. Generally, the impingement may be caused by an overgrowth on an edge of the acetabulum, or pincer impingement, or by an overgrowth on the femoral head of the femur, or cam impingement. Both forms of impingement may be treated using resectional surgery to remove the overgrowth from the affected bones and to restore the full range of motion of the joint. With respect to cam impingement, for instance, an overgrowth on the femur may be resected to restore the sphericity of the femoral head and to enable the femoral head to pivot against the acetabulum without any impingement.

Although most impingement conditions may be successfully treated using currently existing surgical means, a substantial amount of detailed planning must precede the surgical procedure in order to ensure proper and efficient removal of the overgrowth. In cam impingement conditions, for instance, surgeons must pre-operatively determine a plan to recover or recreate the sphericity of the femoral head, and further, to ensure a smooth transition between the outer surfaces of the recreated femoral head and the femoral neck. Such planning involves at least the determination of the specific amount of femoral bone to be removed and the specific areas of the femoral head and neck from which the bone is to be removed. Currently, surgeons are capable of determining the degree of a particular cam impingement based on standard measurements taken from a medical image. More specifically, surgeons analyze and diagnose cam impingement conditions based on a relationship between the femoral head and neck, or an alpha angle, that is visually determined from images provided by an X-ray device, a computer tomography (CT) device, a magnetic resonance imaging (MRI) device, or the like. For example, based on the axial cross-sectional image typically taken through the center of the femoral head, as shown in FIG. 1, surgeons may define the alpha angle α as the angle measured between the neck axis NA of the femur and the line connecting the head center HC with a deviation point p. The head center HC is defined as the center of a circle or sphere S that approximates the femoral head. The neck axis NA is defined as the axis through the center of the femoral neck, or neck center NC, and the head center HC. The deviation point p is defined as the point where the outer surface of femoral head deviates from or exits the approximating sphere S.

By conventional standards, if the alpha angle is greater than 50-55°, a cam impingement may be diagnosed. This provides the surgeon with some standard measure with which to proceed. However, the surgeon is still left with less conventional means for determining the specific volume and areas of the femur that need to be removed during surgery. While advanced three-dimensional imaging devices and computer-aided surgical systems may provide some assistance during the stages of planning and performing surgery, the limitations in visibility and the lack of clear access to the pathologic joint introduce other setbacks. For instance, it may be difficult for the surgeon to visually plan or model the specific dimensions and locations of the resection volume based purely on a series of medical images. Even once a surgical plan is determined, there may still be difficulties in properly and efficiently communicating the specific dimensions and/or locations of the resection volume to a computer-aided system or a haptic- or robot-guided surgical device. Such difficulties and the lack of convention in planning for impingement surgery may place a significant burden on surgeons in the field, and further, may cause impingement surgery in general to be conducted inefficiently and inconsistently.

Accordingly, there is a need to streamline and further facilitate the planning process for surgical treatment of orthopedic impingement conditions. Moreover, there is a need for a computer-aided system or method which provides more conventional, more efficient and more accurate measures for modeling the resection volume prior to surgery.

SUMMARY OF THE DISCLOSURE

In one aspect of the present disclosure, a method for determining a resection volume of a pathologic femur having a femoral head and a femoral neck is provided. The method may determine a first point of a desired contour based on a pathologic alpha angle of the pathologic femur, determine a second point of the desired contour based on a desired alpha angle of the pathologic femur, determine a third point of the desired contour on the femoral neck of the pathologic femur, and generate a resection volume of the pathologic femur based on the first, second and third points of the desired contour.

In another aspect of the disclosure, a method for determining a resection volume of a pathologic femur having a femoral head and a femoral neck is provided. The method may receive medical images of the pathologic femur from a medical imaging device, determine landmarks of the pathologic femur based on the medical images, determine at least a first contour point corresponding to a pathologic alpha angle and a second contour point corresponding to a desired alpha angle, determine a morphing region on the pathologic femur, and generate a resection volume based on the first contour point, the second contour point and the morphing region.

In yet another aspect of the disclosure, a system for resectioning a pathologic femur having a femoral head and a femoral neck is provided. The system may include at least one medical imaging device configured to output medical images of the pathologic femur, and a computing device in communication with the medical imaging device. The computing device may include a memory and a processor configured to receive the medical images from the medical imaging device, determine a first point of a desired contour based on a pathologic alpha angle of the pathologic femur, determine a second point of the desired contour based on a desired alpha angle of the pathologic femur, determine a desired morphing region of the pathologic femur, and generate a resection volume of the pathologic femur based on the first point, the second point and the desired morphing region.

DETAILED DESCRIPTION

Reference will now be made in detail to specific embodiments or features, examples of which are illustrated in the accompanying drawings. Generally, corresponding reference numbers will be used throughout the drawings to refer to the same or corresponding parts. Although the following disclosure may make certain references to orthopedic procedures involving hip joints, it should be understood that the subject matter described herein is applicable to other joints in the body, such as, for example, shoulders, elbows, wrists, spines, knees, ankles, and the like.

Figure 1:
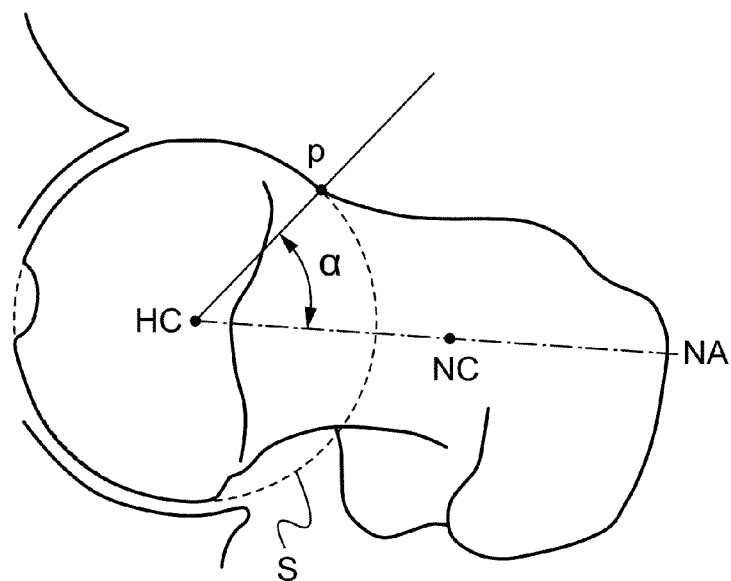
FIG. 1 is an axial cross-sectional view of a hip joint as analyzed by the prior art.
Figure 2:
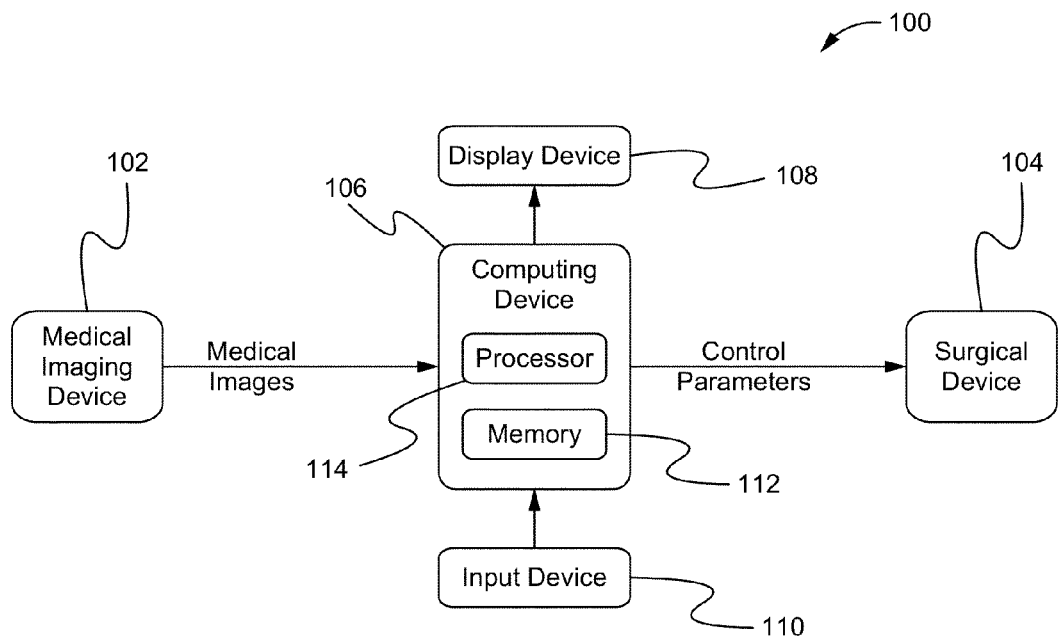
FIG. 2 is a diagrammatic view of one exemplary system for planning and/or performing resectional surgery.

Referring to FIG. 2, one exemplary embodiment of a computer-aided system 100 within which a surgical procedure may be planned or performed is provided. The system 100 shown may be used to plan or perform, for example, femoral acetabular impingement (FAI), or more particularly, cam impingement surgery. The system 100 may also be used to plan or perform other applicable orthopedic procedures. As shown, the system 100 may include one or more medical imaging devices 102, one or more surgical devices 104, and a computing device 106 in communication with each of the medical imaging device 102 and the surgical device 104. The computing device 106 may receive medical images from a medical imaging device 102 to be used during surgical planning. The computing device 106 may also refer to the medical images as reference while communicating control parameters or commands to a surgical device 104 during a surgical procedure.

The medical imaging device 102 of FIG. 2 may include X-ray devices, computed tomography (CT) devices, magnetic resonance imaging (MRI) devices, fluoroscopic devices, ultrasound devices, or any other suitable imaging device that may be used to capture two-dimensional images and/or three-dimensional models of a pathologic structure. For the purposes of cam impingement surgery, for example, the medical imaging device 102 may include at least a CT device configured to capture two-dimensional slices or views of the hip joint. More specifically, the CT device 102 may be used to capture axial and/or coronal cross-sections of the femur including the femoral head and the femoral neck. Axial as well as coronal cross-sections may be taken from a proximal or superior end to a distal or inferior end of the femur at a substantially high resolution, for example, in increments of approximately 1 mm. The captured medical images may then be stored locally at the medical imaging device 102 and/or communicated to the computing device 106 for further analysis. Based on the analysis of the medical images and any user modifications thereof, the computing device 106 may further communicate the appropriate control parameters or commands by which to operate or guide the surgical device 104 during the surgical procedure.

The surgical device 104 of FIG. 2 may include any combination of surgical tools for use on an anatomical structure including burrs, drills, probes, saws, cameras, scopes, irrigation devices, suction devices, radiotherapy devices, and the like. The surgical device 104 may further provide a mechanical or an electromechanical apparatus with which to autonomously navigate or at least partially guide the surgical tool through the anatomy during a surgical procedure. For example, the surgical device 104 may include computer-aided and/or haptic- or robot-guided surgical tools that enable substantially autonomous operation of the surgical tool or provide the user with at least some manual operation of the surgical tool. In fully autonomous applications, the surgical device 104 may be configured to operate solely based on preconfigured control parameters or commands provided by the computing device 106. In other applications, such as haptic-guided applications, the surgical device 104 may be configured to guide or provide sensory feedback to the user in a manner adapted to limit certain movements and/or operations of the surgical tool according to the control parameters generated by the computing device 106. Accordingly, the control parameters communicated to the surgical devices 104 may correspond to three-dimensional spatial data associated with the desired resection volume, a series of two-dimensional data pertaining to cross-sectional slices of the resection volume, or the like.

The computing device 106 of FIG. 2 may additionally be in communication with each of a display device 108 for displaying the medical images captured by the medical imaging device 102, and an input device 110 for receiving any additional input from the user, such as a surgeon, or the like. The display device 108 may include a liquid crystal display (LCD), a cathode ray tube (CRT) display, a plasma screen, a touch screen, or any other output device that enables the user to view the medical images of the pathologic structure. Specifically, the medical images displayed at the display device 108 may be represented as two- or three-dimensional renderings of the pathologic structure. In an application directed toward cam impingement surgery, for example, the display device 108 may be used to display one or more of a plurality of axial and/or coronal cross-sections of the pathologic femur. The input device 110 may include a keyboard, a mouse, a trackball, a touch screen, a touch pad, a microphone, a dial, a switch, a button, a camera, or any other input device that enables the user to input information into the computing device 106. The computing device 106 may also include hardware, such as memory 112 for locally and at least temporarily storing data, and a processor 114 for executing a preprogrammed set of steps or an algorithm. The data stored in the memory 112 may include a collection of medical images provided by one or more medical imaging devices 102, as well as any other data that may be relevant to the instant pathologic structure. The memory 112 may also be configured to locally store the algorithm or any other data that may be required by the processor 114 in order to execute steps of the algorithm. In alternative embodiments, the computing device 106 may include a controller, a microcontroller, a form of programmable read-only memory (PROM), a field programmable gate array (FPGA), or any other suitable arrangement of circuitry that may be configured to function according to a predefined series of steps. Based on the medical images provided by the medical imaging devices 102 and any input provided by the user, the processor 114 of the computing device 106 may be configured to generate a series of control parameters by which the surgical devices 104 may perform or guide the user in performing a surgical procedure.

Figure 3:
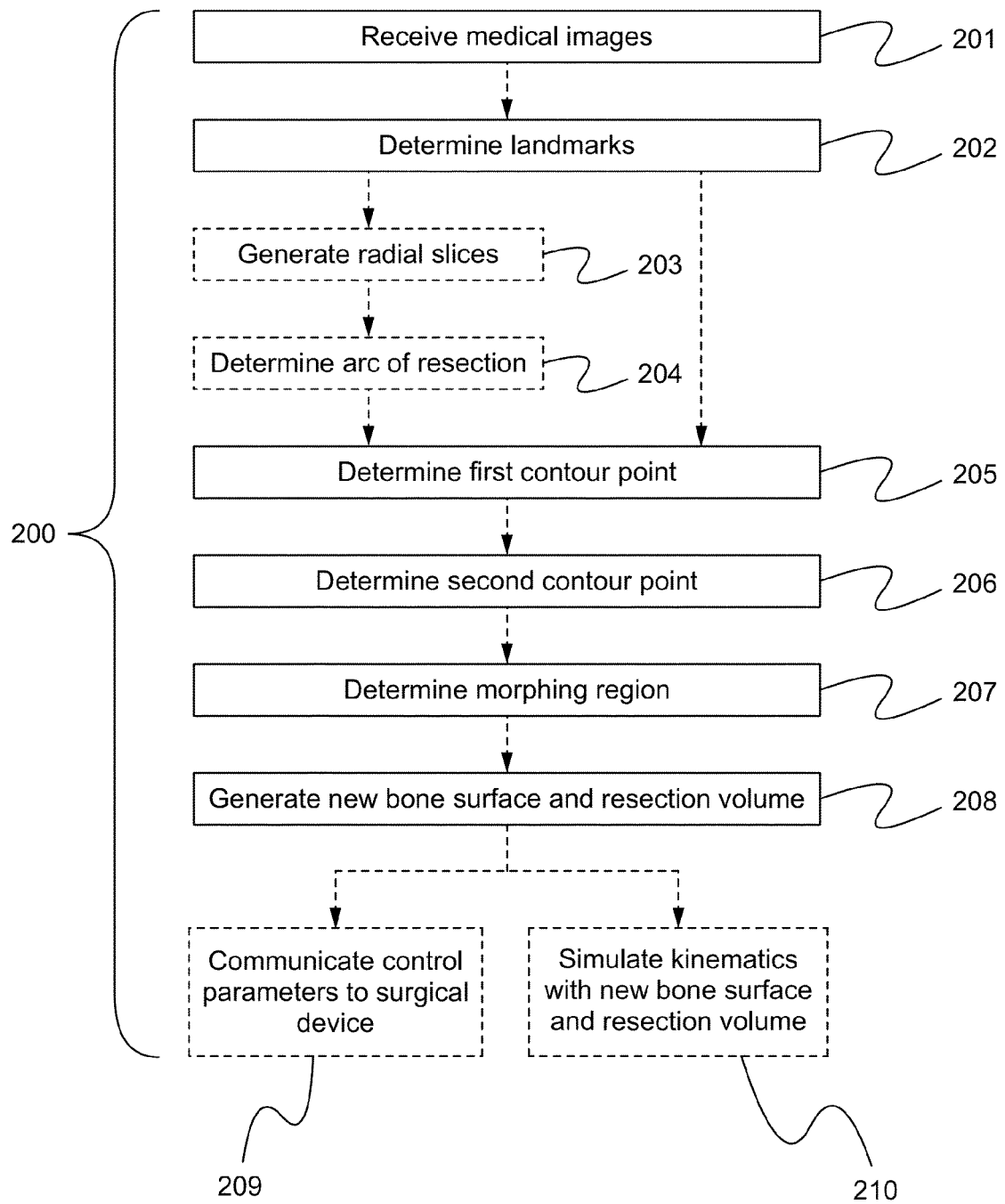
FIG. 3 is a flow diagram of exemplary methods for determining a resection volume of a pathologic bone structure.
Figure 4:
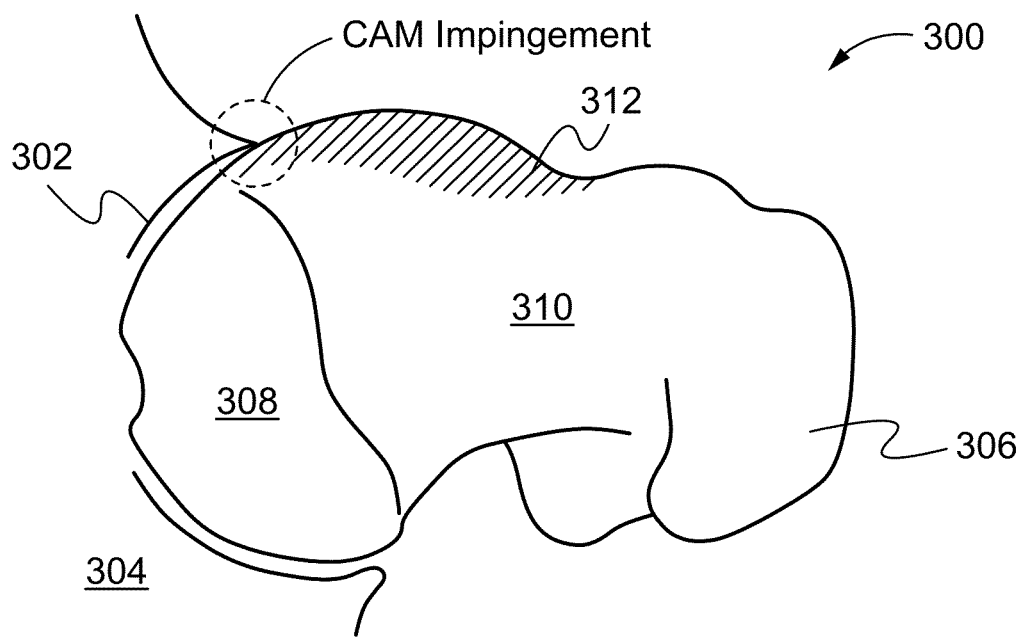
FIG. 4 is an axial cross-sectional view of a cam impingement on a pathologic femur.

Turning to the embodiment of FIG. 3, an exemplary method or algorithm 200 by which the computing device 104 and its associated processor 114 may, for example, automatically assist with the planning or performing of cam impingement surgery is provided. Specifically, the computing device 104 and its associated processor 114 may be preprogrammed with software to function according to steps 201-210 shown in FIG. 3. In an optional step 201, the computing device 106 may receive medical images of a pathologic hip joint 300, as shown in FIG. 4, showing the acetabulum 302 of the pelvis 304, femur 306 as well as the femoral head 308 and neck 310 pivotally attaching the femur 306 to the acetabulum 302. More specifically, the medical images may include a plurality of cross-sectional slices or axial views of the hip joint 300 as provided by a CT medical imaging device 102. From the axial view of FIG. 4, it may be possible to determine the location of the overgrowth 312 on the femur 306 and the location of the cam impingement, or where the overgrowth 312 impinges with the acetabulum 302. The medical images may also include coronal views or any other cross-sectional slices which adequately display the relevant areas of the hip joint 300. In still further modifications, the medical images may include lateral views of the hip joint 300.

Figure 5:
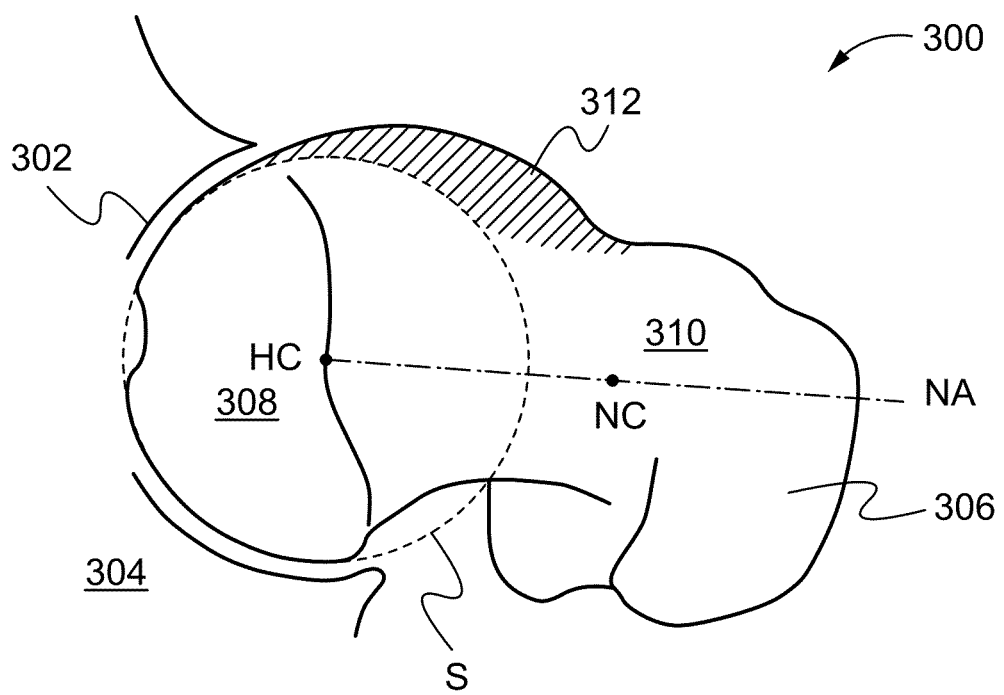
FIG. 5 is an axial cross-sectional view of a pathologic femur and landmarks thereof.

According to step 202 of the algorithm 200 of FIG. 3, the computing device 106 may be configured to determine specific landmarks within the femur 306 based on the medical images received in step 201. As shown for example in FIG. 5, landmarks corresponding to at least the femoral head center HC, the femoral neck center NC and the neck axis NA may be selected or determined from the axial CT images. The head center HC may be defined as the center of a circle or sphere S which approximates the outer surface of the femoral head 308. The parameters of the fitted sphere S may be determined based on a three-dimensional model of the femur 306. More specifically, a plurality of coordinate points corresponding to the outer surface of the femoral head 308 may be applied to a least squares sphere fitting sub-algorithm, or the like, to construct the sphere S that best approximates the femoral head 308 and to determine the head center HC based on the centermost point thereof. Alternatively, the head center HC may be derived based on the calculated centermost point of a plurality of two-dimensional circles approximating the cross-sectional perimeters of the femoral head 308. In still further alternatives, the head center HC may be derived by calculating the centermost point of an outer surface of the femoral head 308 that is detected and approximated using an automatic edge detection filter, or the like. The neck center NC may be defined as the common cross-sectional midpoint of the femoral neck 310 as determined from two or more orthogonal planes, such as axial and coronal slices thereof. Furthermore, the neck axis NA may be defined as the axis intersecting both the head center HC and the neck center NC.

Figure 6:
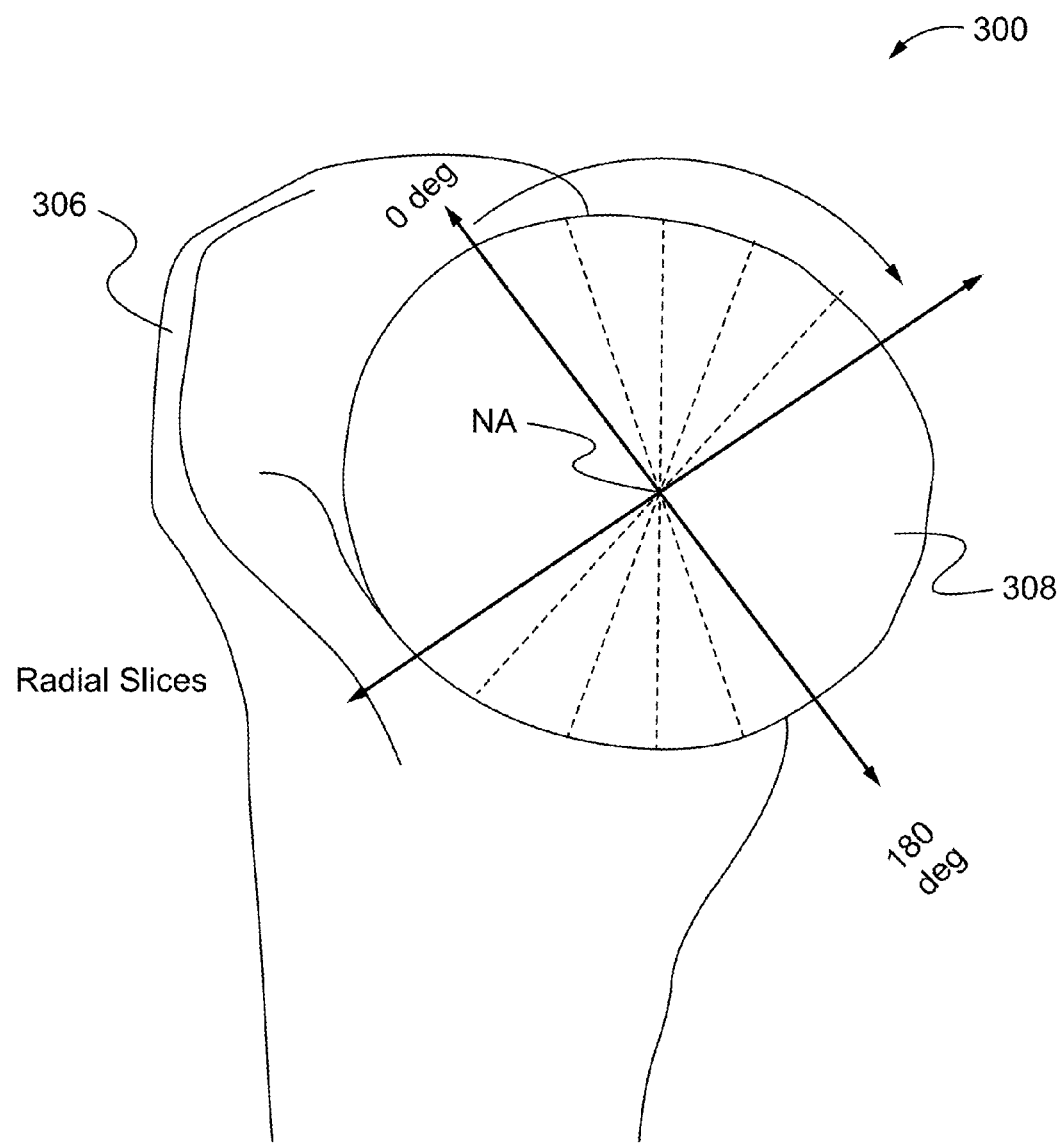
FIG. 6 is a lateral view of a pathologic femur and radial slices thereof.
Figure 7:
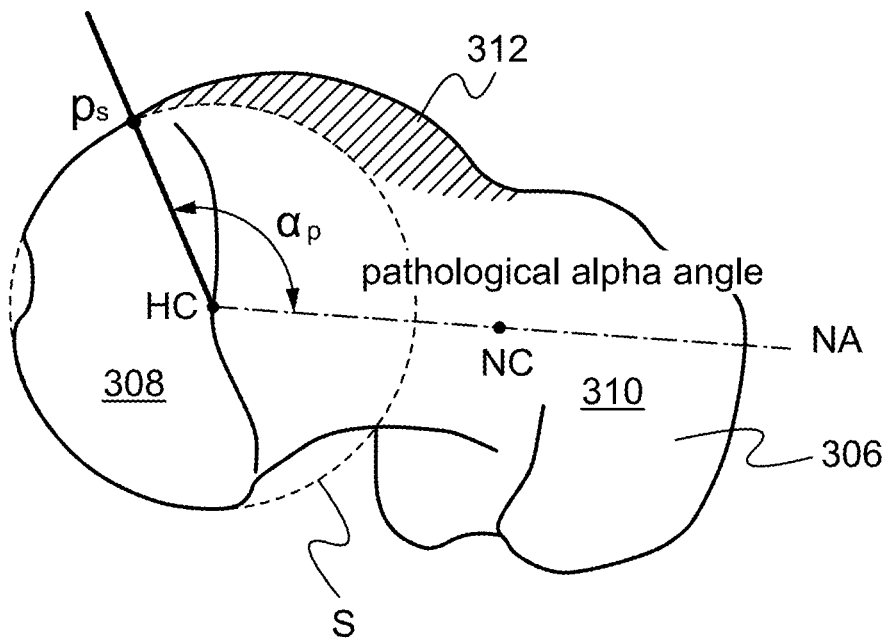
FIG. 7 is an axial cross-sectional view of a pathologic femur and a pathologic alpha angle thereof.
Figure 8:
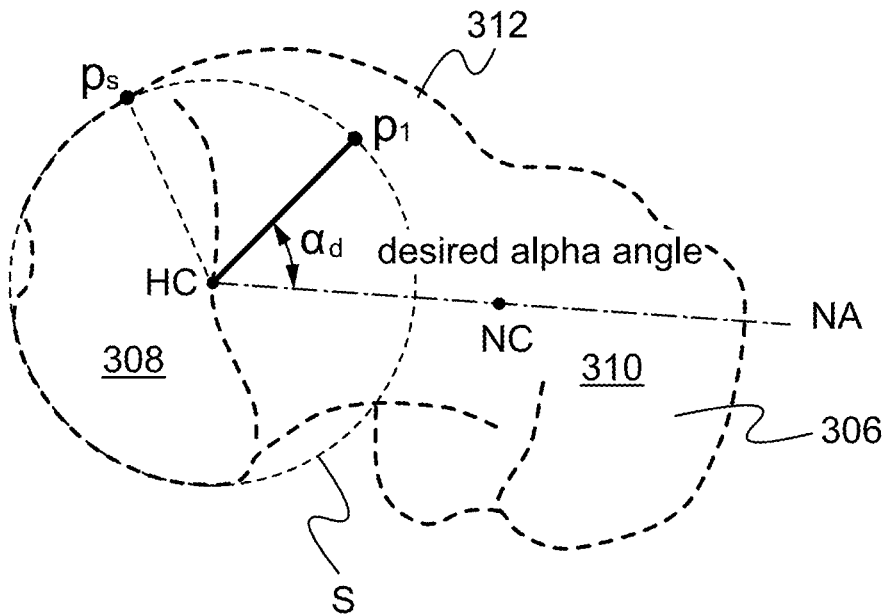
FIG. 8 is an axial cross-sectional view of a pathologic femur and a desired alpha angle thereof.

Once the landmarks have been determined, the computing device 106 may generate a series of desired resection contours from which a resection volume may ultimately be constructed. Moreover, each resection contour may be constructed using two or more contour points that are defined within each radial slice of the femoral head 308. As shown in FIG. 6, for example, the algorithm 200 may optionally configure the computing device 106 to generate a plurality of radial slices of the femoral head 308 within a range of angles about the neck axis NA in step 203. The range of angles may be determined within a coordinate system that is manually defined by a user, or automatically defined by the algorithm 200 based on, for example, the femoral epicondyles and the head center HC. For each radial slice of the femoral head 308, the algorithm 200 may configure the computing device 106 to determine the pathologic alpha angle $\alpha_p$. As illustrated in FIG. 7, the pathologic alpha angle $\alpha_p$ may be defined by the angle between the neck axis NA and a line connecting the head center HC with a point $p_s$ on the approximating sphere S. The point $p_s$ may be defined as the point where the femoral head 308 first deviates from the approximating sphere S, and thus, may be indicative of where the overgrowth 312 originates on the femoral head 308. Based on the pathologic alpha angles $\alpha_p$, the computing device 106 may determine the radial slice having the largest pathologic alpha angle $\alpha_y$, and further, determine or aid in determining the desired alpha angle $\alpha_d$ corresponding thereto. More specifically, the computing device 106 may enable the user to input a desirable alpha angle $\alpha_d$ appropriate for alleviating the impingement condition of the femur 306. As shown in FIG. 8, for example, the surgeon may input a desired alpha angle $\alpha_d$ of approximately 50°, or any other alpha angle that may be considered ideal for a hip joint according to conventional standards. The values provided by the user and received by the computing device 106 may be scalar input values, vector input values, or any other form or combination of values that may appropriately be interpreted by the computing device 106 as the desired alpha angle $\alpha_d$. In alternative embodiments, the computing device 106 may be configured to determine the desired alpha angle $\alpha_d$ corresponding to each of the radial slices generated in step 203.

Figure 9:
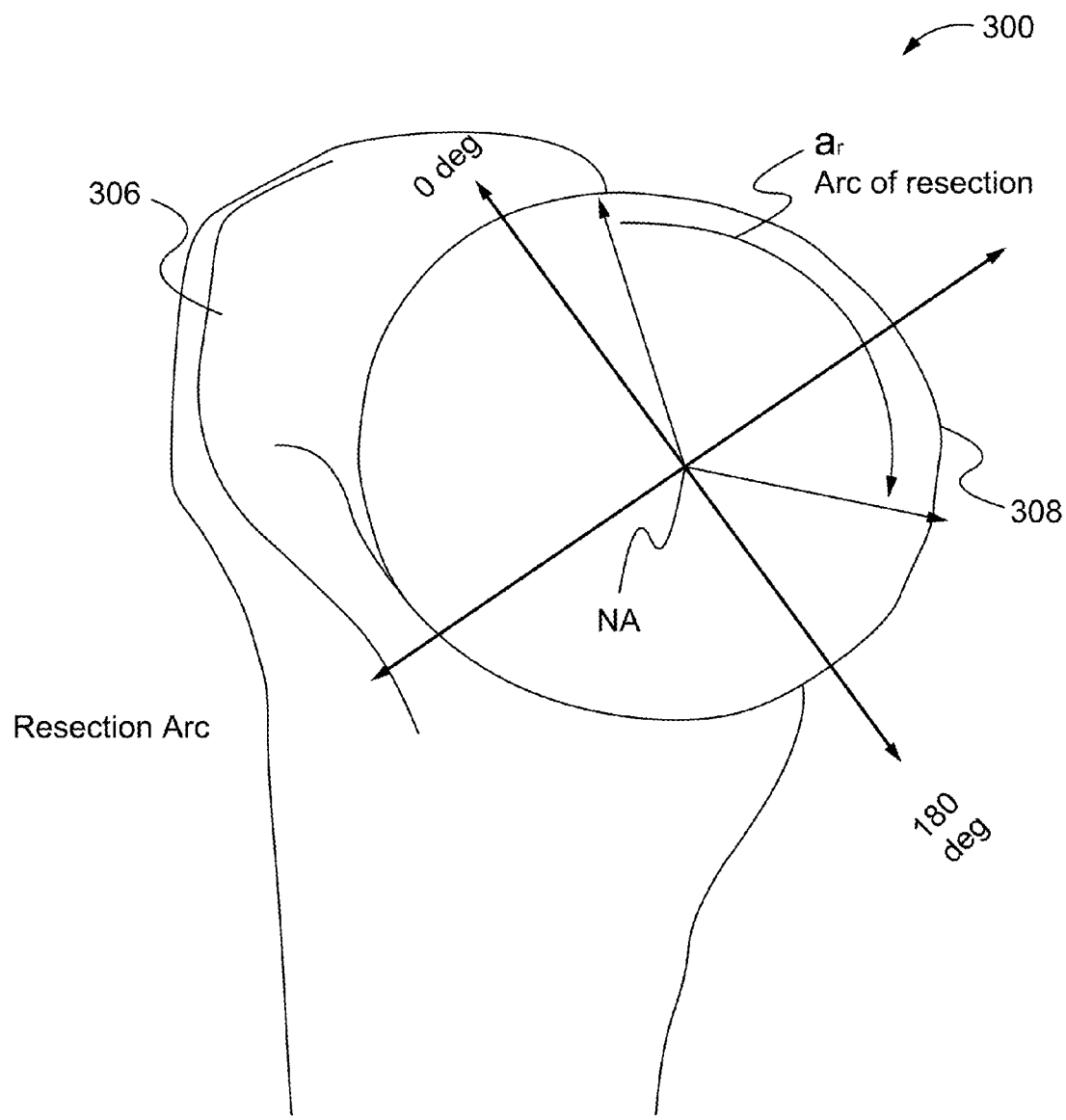
FIG. 9 is a lateral view of a pathologic femur and an arc of resection thereof.
Figure 10:
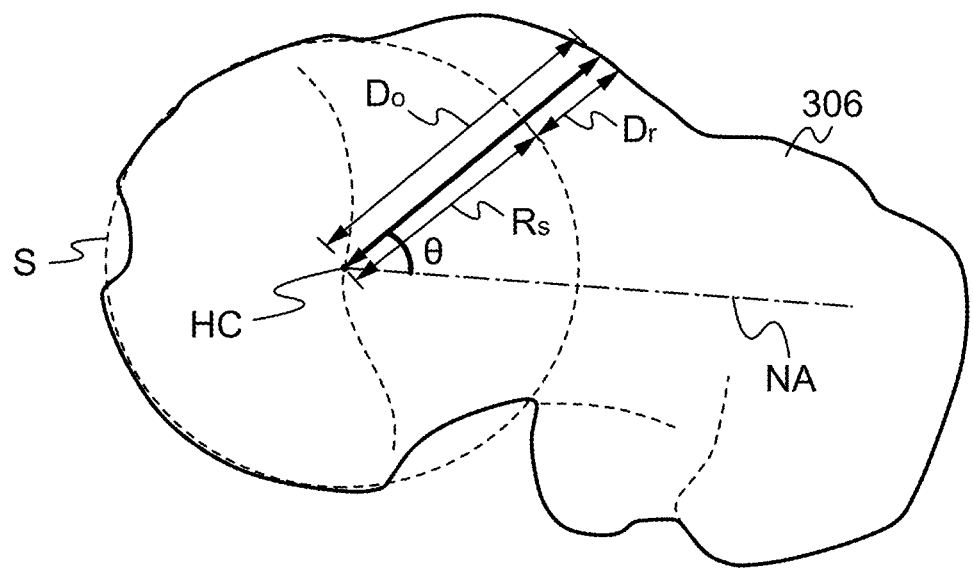
FIG. 10 is an axial cross-sectional view of the pathologic femur and arc of resection of FIG. 9.
Figure 11:
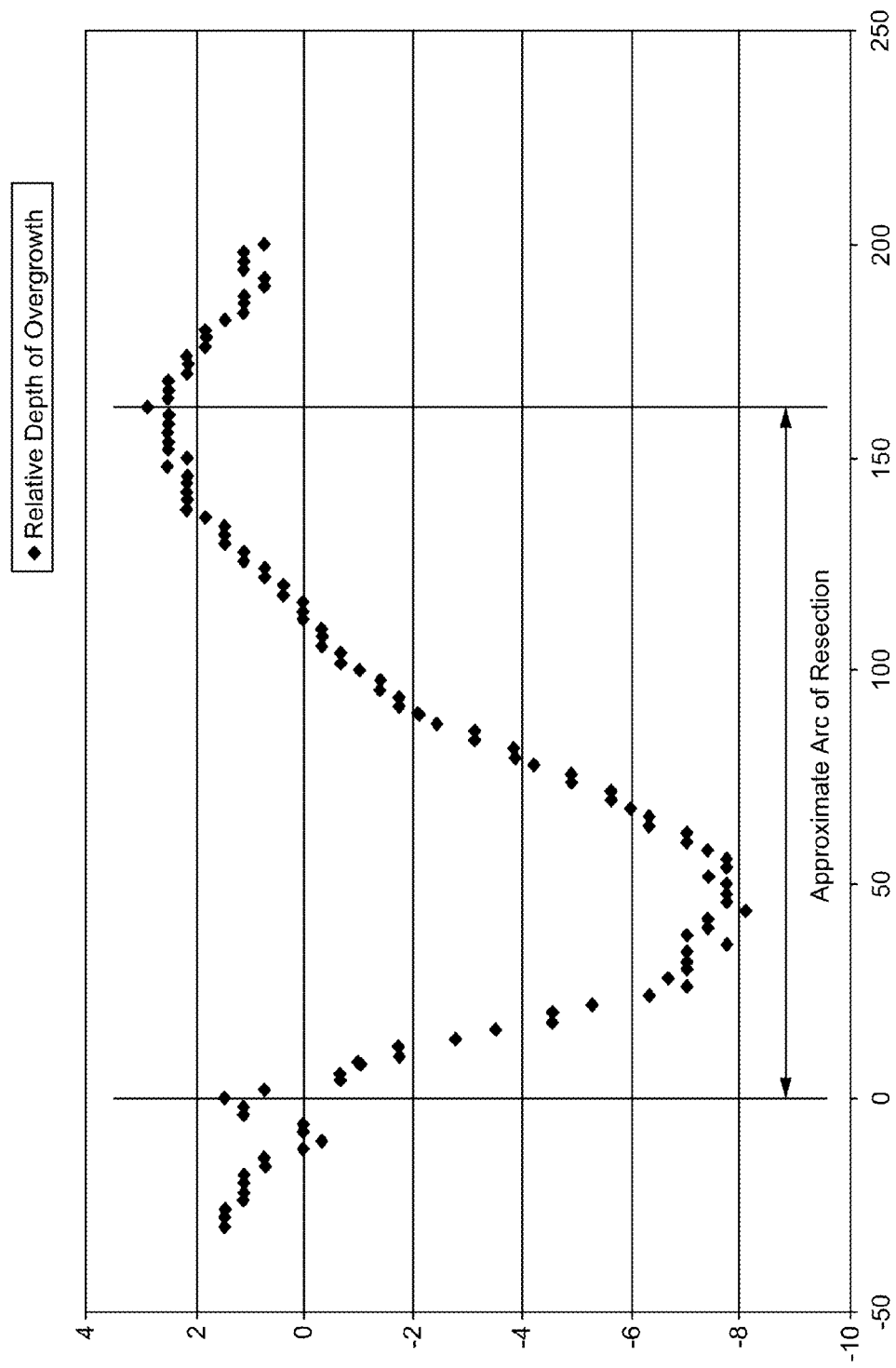
FIG. 11 is a graphical view of the relative depth of an overgrowth of a pathological femur as compared with an approximating sphere.

In step 204 of FIG. 3, the computing device 106 may optionally be configured to automatically determine or aid a user in manually determining an arc of resection $a_r$, as shown in FIG. 9. The arc of resection $a_r$ may be determined based on measurements of the depth of a particular overgrowth taken relative to the approximating sphere S, or the relative depth $D_r$, in each of the individual radial slices generated in step 203. As shown in FIG. 10, for example, the relative depth $D_r$ of the overgrowth in each radial slice may be determined based on a difference between the radius $R_s$ of the approximating sphere S and an overall depth $D_0$ of the overgrowth. The overall depth $D_0$ may be measured as the distance between the head center HC and the surface of the overgrowth at a predefined angle θ with the neck axis NA. As shown in FIG. 10, the angle θ may be predefined as approximately 45°, or within an approximate range thereabout. In the particular embodiment shown, the relative depth $D_r$ of the overgrowth may be numerically quantified by approximations using the relationship, $D_r = R_s - D_o$. The resulting relative depth $D_r$ of each radial slice may be graphically represented, as further shown in FIG. 11. As shown, positive indices of the relative depth $D_r$ may correspond to surfaces of the femur 306 where the overall depth $D_o$ is less than the radius $R_s$ of the approximating sphere S, while negative indices may correspond to surfaces of the femur 306 where the overall depth $D_o$ is greater than the radius $R_s$ of the approximating sphere S. The magnitudes of the numerical indices in FIG. 11 may be indicative of the general degree of offset between the surface of the femur 306 and the approximating sphere S. Based on such indices, the computing device 106 may automatically determine or aid a user in manually determining the arc of resection $a_r$, or the range of radial slices which exhibit substantial overgrowths and are in need of attention. For example, in the embodiment of FIG. 11, the arc of resection $a_r$ may be selected to include the range of radial slices which exhibit relative depth values $D_r$ having negative indices and substantially high magnitudes, or approximately between the angles of 0° and 160° about the neck axis NA.

Figure 12:
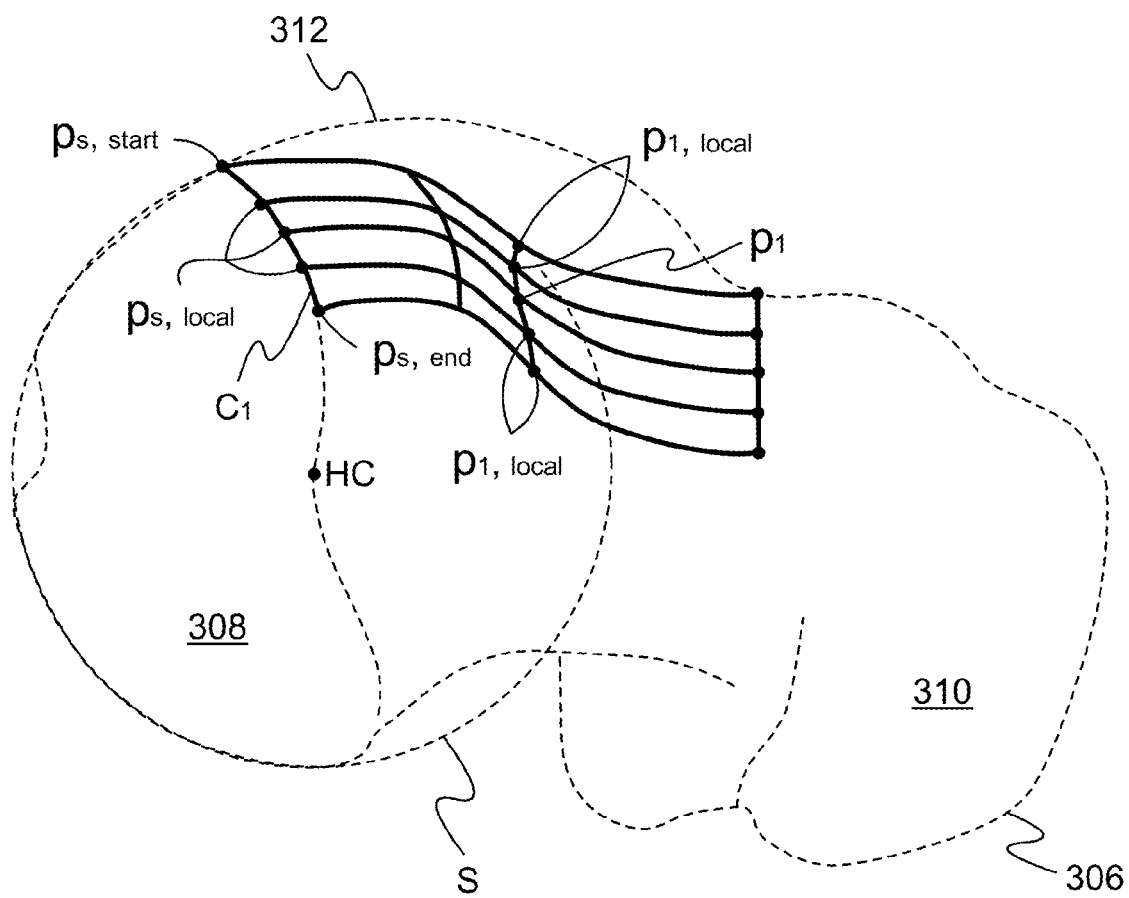
FIG. 12 is an axial cross-sectional view of a pathologic femur and a plurality of resection contours thereof.

Once the arc of resection $a_r$ has been defined, the computing device 106 may proceed in determining the first contour point $p_s$ of the resection contour in each of the radial slices within the arc of resection $a_r$ in step 205. More specifically, the algorithm 200 may configure the computing device 106 to initially determine the first contour points $p_{s,start}$ and $p_{s,end}$ corresponding to the first and last radial slices located within the arc of resection $a_r$, for instance, at 0° and 160° of FIG. 11, respectively. As illustrated in FIG. 12, each of the first contour points $p_{s,start}$ and $p_{s,end}$ may be defined as the point of intersection between the pathologic alpha angle $α_p$ and the surface boundary of the femur 306 within the respective radial slice. In order to determine the intermediate or local first contour points $p_{s,local}$ corresponding to the radial slices located between the first and last radial slices, the computing device 106 may generate, for example, the interpolation curve $C_1$ shown in FIG. 13. Among other things, curve $C_1$ may be interpolated based at least partially on the first contour points $p_{s,start}$ and $p_{s,end}$ the arc of resection $a_r$, the neck axis NA, approximating sphere S, and the like. More specifically, curve $C_1$ may be used to approximate the locations of local first contour points $p_{s,local}$ between the first contour point $p_{s,start}$ of the first radial slice and the first contour point $p_{s,end}$ of the last radial slice. Rather than using such interpolation schemes, the algorithm 200 of the computing device 106 may alternatively be modified to individually determine the local first contour point $p_{s,local}$ corresponding to each intermediate radial slice in the same manner by which each of the first contour points $p_{s,start}$ and $p_{s,end}$ were determined.

Figure 13:
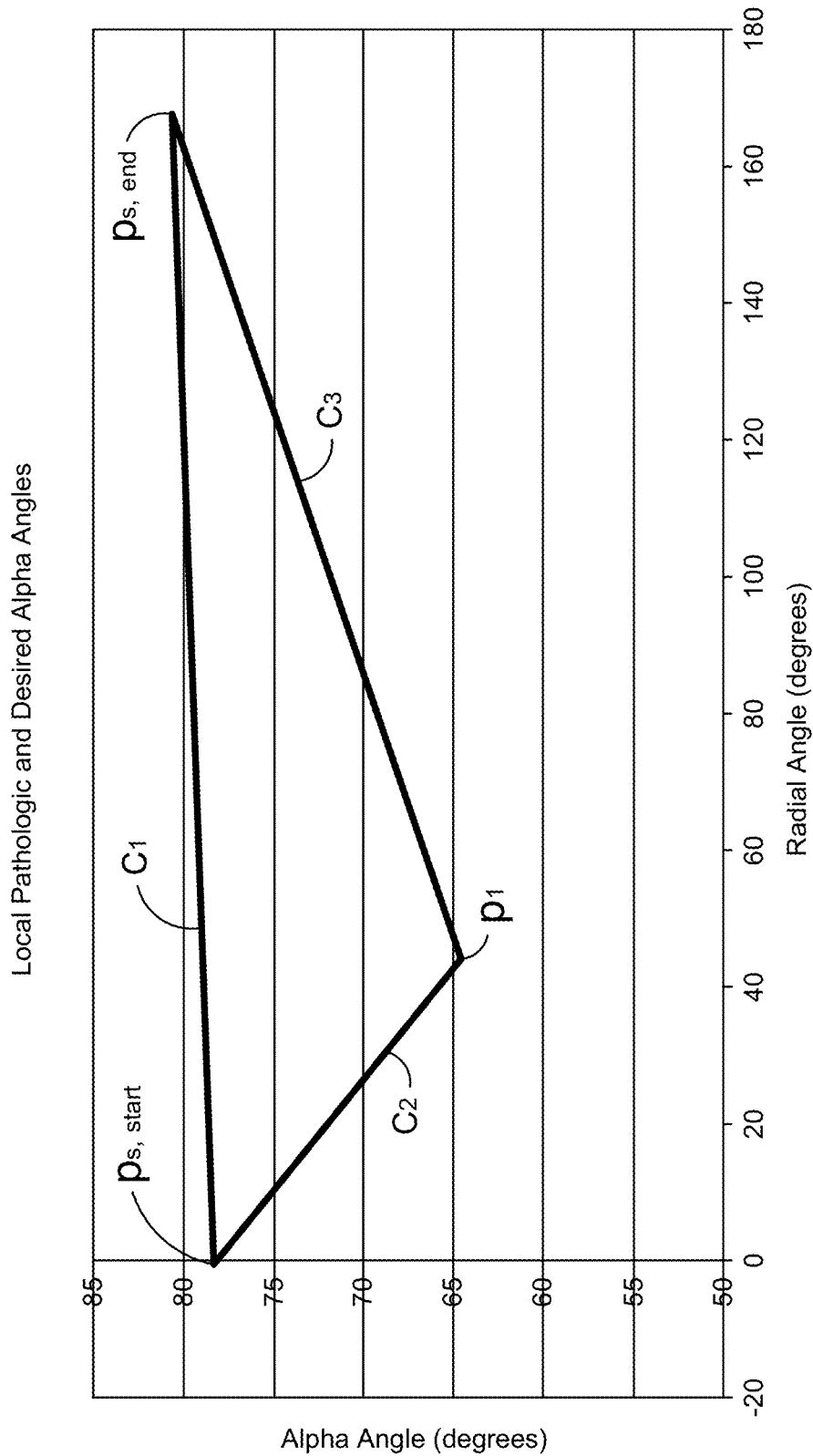
FIG. 13 is a graphical view of first and second contour points and local interpolations thereof.

As shown in step 206 of FIG. 3, the computing device 106 may additionally determine a second contour point $p_1$ of the resection contour based at least partially on the desired alpha angle $α_d$. In alternative embodiments, the second contour point $p_1$ may indicate the end of a resection of a particular slice. Similar to first contour points $p_{s,start}$ and $p_{s,end}$, the second contour point $p_1$ may be defined as the point of intersection between desired alpha angle $α_d$, previously determined during step 203, and the surface boundary of the pathologic femur 306. Moreover, the second contour point $p_1$ may correspond to the radial slice having the largest pathologic alpha angle $α_p$, for example, the radial slice located at 40° according to FIG. 13. The algorithm 200 may further configure the computing device 106 to determine local second contour points $p_{1,local}$ corresponding to other remaining radial slices within the arc of resection $a_r$ as indicated in FIG. 12. For example, the computing device 106 may generate the interpolation curve $C_2$, as shown in FIG. 13, between the first contour point $p_{s,start}$ belonging to the first radial slice and the second contour point $p_1$, so as to approximate the locations of the local second contour points $p_{1,local}$ in the radial slices situated between 0° and 40°. Similarly, the interpolation curve $C_3$ may be generated between the first contour point $p_{s,end}$ belonging to the last radial slice and the second contour point $p_1$, so as to approximate the locations of the local second contour points $p_{1,local}$, for example, in the radial slices situated between 40° and 160° according to FIG. 13. In alternative embodiments, the computing device 106 may determine local second contour points $p_{1,local}$ for each of the intermediate radial slices in the same manner by which the second contour point $p_1$ was initially determined.

In step 207 of FIG. 3, the computing device 106 may additionally determine a desired morphing region or a third contour point $p_2$ on the femoral neck 310 with which the resection contour of the first and second contour points $p_s$, $p_1$ may smoothly merge or conform. For example, in each radial slice disposed within the arc of resection $a_r$, the third contour point $p_2$ may be automatically, or manually by the user, defined as the point on the surface boundary of the femoral neck 310 that is nearest to the neck axis NA. Optionally, the user may manually select the desired location of the third contour point $p_2$ for one or more of the radial slices. Accordingly, for each radial slice within the selected arc of resection $a_r$, the computing device 106 may be configured to define at least two contour points, for example, the first contour point $p_s$ that is derived from the pathological alpha angle $α_p$, and the second contour point $p_1$ that is derived from the desired alpha angle $α_d$. The computing device 106 may additionally be configured to define a morphing region or a third contour point $p_2$ that is based on the surface boundary of the femoral neck 310. Moreover, for each radial slice, the computing device 106 may designate the first contour point $p_s$ as the starting point of the resection, the second contour point $p_1$ as the intermediate point of the resection, and the third contour point $p_2$ as the ending point of the resection. By combining the resection contours of each radial slice within the arc of resection $a_r$, the algorithm 200 may be able to simulate the new bone surface on a representation of the pathologic femur 306.

The resection contours and associated contour points $p_s$, $p_1$, $p_2$ previously obtained may be derived using other schemes or techniques. Such modifications will be apparent from the above description to those skilled in the art without departing from the scope of the present disclosure. For example, rather than defining resection contours based on radial slices, the method or algorithm 200 of FIG. 3 may be configured to define resection contours using the cross-sectional slices or axial views of the femur 306 provided by the CT medical imaging device 102 during step 201. More specifically, the computing device 106 may be configured to omit steps 203 and 204 of FIG. 3 and proceed to determine the relevant contour points of the resection contours based on the medical images received in step 201 and the landmarks determined in step 202.

In step 205 of such a modifiable algorithm 200, the computing device 106 may be configured to determine the first contour point $p_s$ of the desired resection contour based on the pathologic alpha angle $\alpha_p$ of the femur 306. As shown in FIG. 7, the pathologic alpha angle $\alpha_p$ may be determined by measuring the angle between the neck axis NA and the line connecting the head center HC with a point $p_s$ on the approximating sphere S. The point $p_s$ may be defined as the point where the femoral head 308 first deviates from the approximating sphere S, and thus, may be indicative of where the overgrowth 312 originates on the femoral head 308. Furthermore, the pathologic alpha angle $\alpha_p$ and the associated first contour point $p_s$ may be determined for each of a plurality of cross-sectional slices taken from a superior end of the femoral head 308 to an inferior end of the femoral head 308 or neck 310 at a substantially high resolution. The first contour point $p_s$ for each axial image may be defined as the point where the femoral head 308 deviates from corresponding cross-sections of the approximating sphere S in each slice. The first set of contour points $p_s$ that are collected from the individual axial images may be reconstructed to form a lateral band of points $p_s$ defining where the overgrowth 312 originates on the femoral head 308 in the three-dimensional domain.

In step 206 of FIG. 3, the computing device 106 may be configured to determine the second contour point $p_1$ of the desired contour based on the desired alpha angle $\alpha_d$ of the femur 306. More specifically, the computing device 106 may enable the user or surgeon to input a desirable alpha angle $\alpha_d$ suited to alleviate the impingement condition of the femur 306. As shown in FIG. 8, for example, the surgeon may input a desired alpha angle $\alpha_d$ of approximately 50°, or any other alpha angle that may be considered ideal according to conventional standards. The values provided by the user and received by the computing device 106 may be scalar input values, vector input values, or any other form or combination of values that may be interpreted by the computing device 106 as the desired alpha angle $\alpha_d$. Based on the desired alpha angle $\alpha_d$ selected, the computing device 106 may further determine the second contour point $p_1$. As shown in FIG. 8, the computing device 106 may define the second contour point $p_1$ as the point of intersection between the sphere S approximating the femoral head 308 and the line originating from the head center HC and creating an angle of $a_d$ with the neck axis NA. The second contour point $p_1$ of the resection contour may be indicative of the depth to which the overgrowth 312 of the femoral head 308 may be removed and the desired starting point of the femoral neck 310. As with step 205, the second contour point $p_1$ may also be determined for each of a plurality of cross-sectional images, such as axial CT images, taken throughout the length of the femoral head 308 and neck 310. Together with the first set of contour points $p_s$, the second set of contour points $p_1$ that are collected from each individual image may be reconstructed to form a three-dimensional boundary or depth to which the femoral head 308 may be resected.

Figure 14:
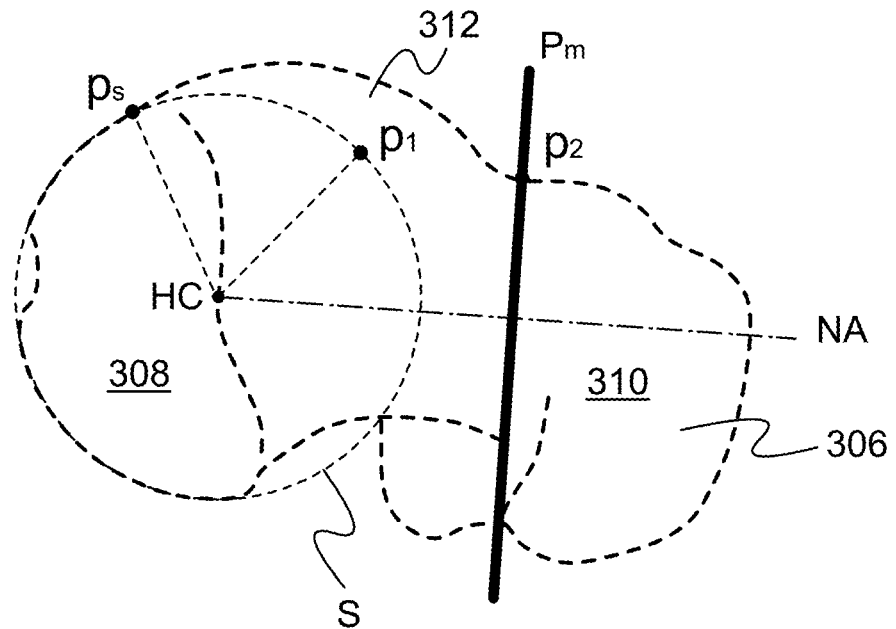
FIG. 14 is an axial cross-sectional view of a pathologic femur and a morphing region thereof.

In step 207 of FIG. 3, the computing device 106 may further be adapted to determine a desired morphing region or a third contour point $p_2$ on the femoral neck 310 with which the desired resection contour of the first and second contour points $p_s$, $p_1$ may smoothly merge. The computing device 106 may enable the user to input the third contour point $p_2$ using the display device 108, input device 110, or combinations thereof. As illustrated in FIG. 14, for example, the computing device 106 may enable the user to select the third contour point $p_2$ on the femoral neck 310 for each of a plurality of cross-sectional slices, such as axial CT images, taken across the length of the femoral neck 310. The resulting third set of contour points $p_2$ that are collected from the individual cross-sectional images may be reconstructed to form a three-dimensional band around the outer circumference of the femoral neck 310 indicating where the resection volume should end. As also shown in FIG. 14, the computing device 106 may alternatively enable the user to select a morphing plane $P_m$ that is perpendicular to the neck axis NA and indicative of where the desired resection contour should merge with the femoral neck 310. The computing device 106 may then determine a three-dimensional set of contour points $p_2$ based on where the morphing plane $P_m$ intersects with the outer surface of the femoral neck 310. In still further alternatives, the computing device 106 may be configured to automatically detect the best morphing plane $P_m$ and/or the third set of contour points $p_2$ without input from the user. For instance, by applying edge detection or other image recognition techniques on the medical images, the computing device 106 may be configured to automatically suggest the most appropriate set of contour points $p_2$ on the femoral neck 310 with which the desired resection contour may morph.

Figure 15:
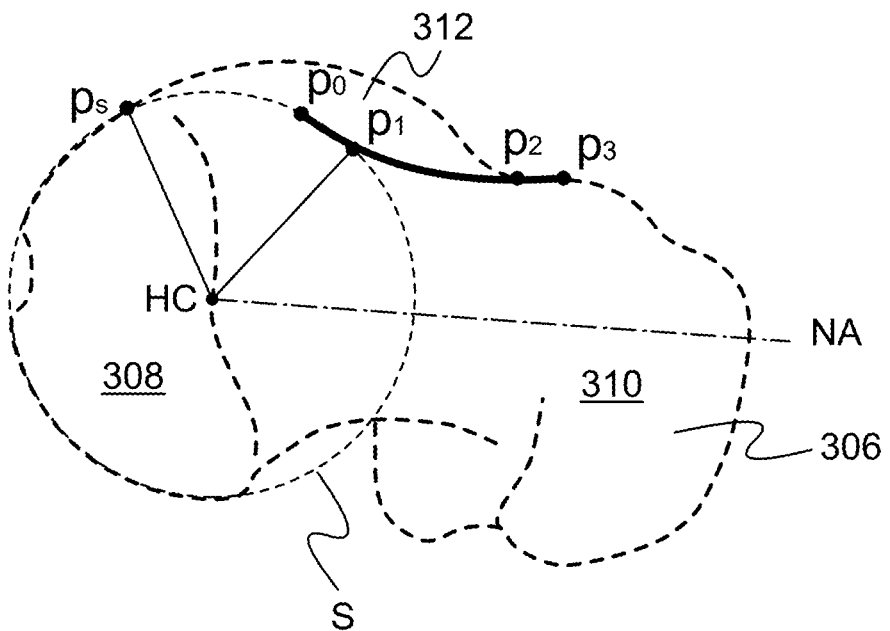
FIG. 15 is an axial cross-sectional view of a pathologic femur and a desired resection contour thereof.
Figure 16:
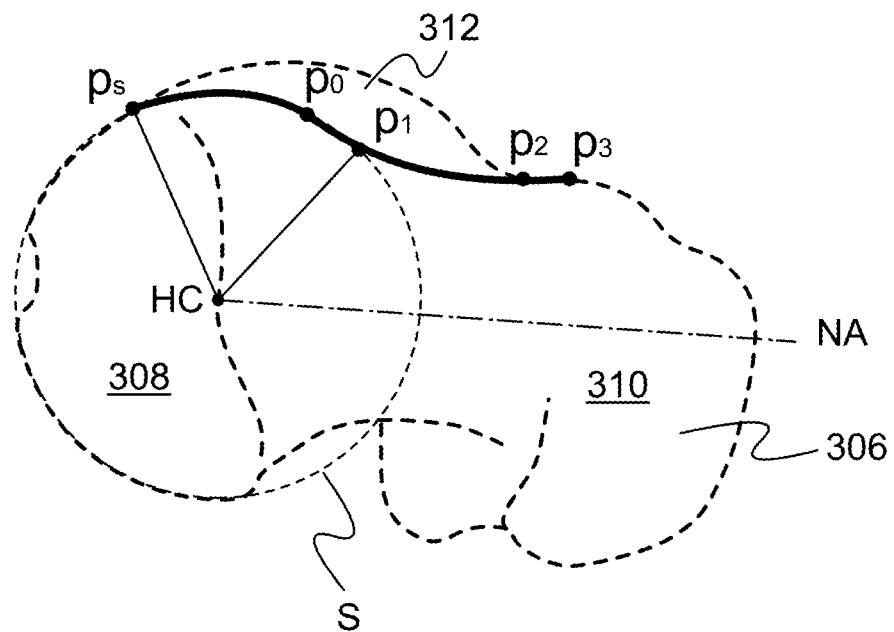
FIG. 16 is an axial cross-sectional view of a pathologic femur and another desired resection contour thereof.

The computing device 106 may thus be configured by any suitable modification of the algorithm 200 of FIG. 3, for example, using radial or axial slices, to derive a desired set of resection contours. Based on the medical images provided in step 201 as well as the parameters determined in steps 202-207, the computing device 106 may further be configured to generate a new bone surface and/or a resection volume according to step 208. More specifically, the computing device 106 may be able to spatially define and superimpose a three-dimensional model of the resection volume to be removed from the pathologic femur 306 onto a three-dimensional model of the femur 306. In one particular embodiment, the computing device 106 may automatically provide one or more additional control points so as to further define the desired resection contour. The computing device 106 may determine a more medial point $p_0$ positioned on the approximating sphere S and in between the first and second contour points $p_s$, $p_1$. As shown in FIG. 15, for example, the contour between the medial point $p_0$ and the second contour point $p_1$ may be disposed generally along the approximating sphere S while conforming to the contour defined by contour points $p_1$-$p_2$. As shown in FIG. 16, for example, the contour between the first contour point $p_s$ and the medial point $p_0$ may similarly be disposed along the approximate sphere S while conforming to the contour defined between contour points $p_0$-$p_2$. In other alternative modifications, the computing device 106 may be configured to enable the user to manually provide one or more additional control points so as to further define the desired resection contour.

Figure 17:
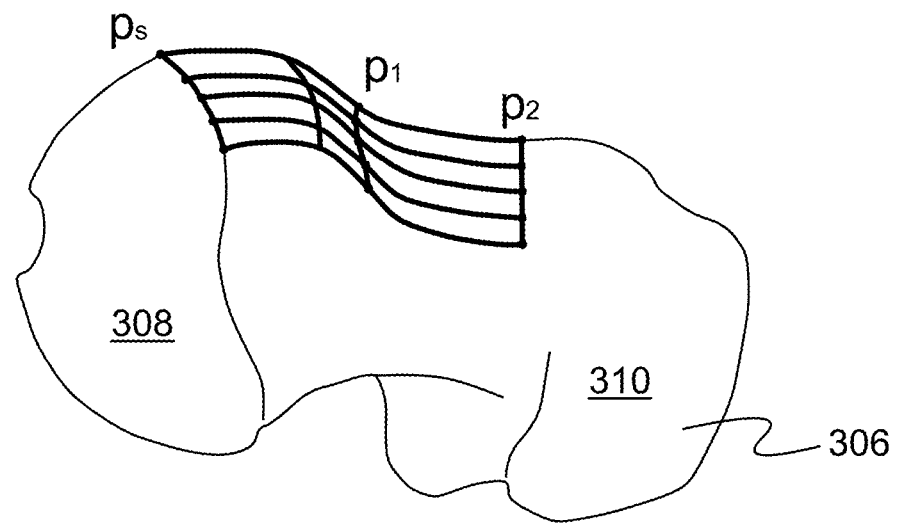
FIG. 17 is an axial view of a pathologic femur and a plurality of desired resection contours thereof.

As further illustrated in FIG. 16, the computing device 106 may additionally or alternatively determine a more lateral point $p_3$ positioned on a more inferior portion of the femoral neck 310. Based on one or more of the additional control points $p_0$, $p_3$ as well as the user-defined contour points $p_1$, $p_2$, the computing device 106 may generate a parametric polynomial curve $p_0$-$p_3$ which coincides with each control and contour point $p_0$, $p_1$, $p_2$, $p_3$ and conforms to the overall desired structure of the femur 306, as illustrated in FIG. 15. As shown in FIG. 16, the parametric polynomial curve $p_0$-$p_3$ may also be joined with one or more segmented contours, such as the contour between points $p_s$-$p_0$, to further define the desired resection contour. The resulting contour, for example, $p_s$-$p_2$ of FIG. 17, may suggest the most appropriate contour by which the femur 306 is to be resected. The computing device 106 may similarly generate corresponding resection contours for all other relevant slices, and radially or axially stack the resection contours to spatially model the new bone surface and/or the resection volume in the three-dimensional domain.

Figure 18:
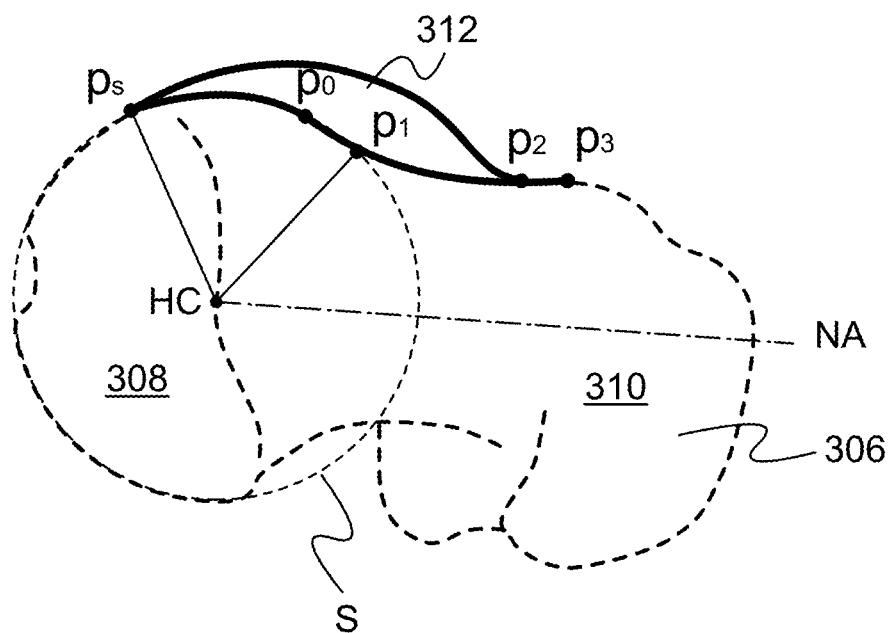
FIG. 18 is an axial cross-sectional view of a pathologic femur and a closed resection contour thereof.
Figure 19:
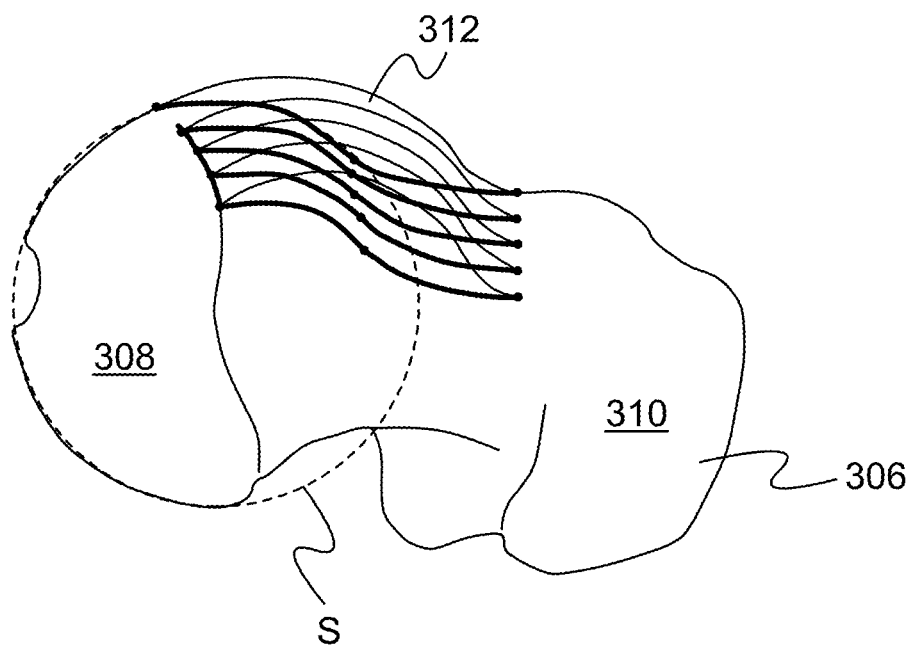
FIG. 19 is an axial view of a pathologic femur and a plurality of closed resection contours thereof.

Furthermore, according to the optional step 209 of FIG. 3, the computing device 106 may be configured to communicate control parameters or commands corresponding to the previously generated new bone surface and/or resection volume to a computer-aided and/or haptic- or robot-guided surgical device 104, for example, as disclosed in commonly assigned U.S. Pat. No. 8,010,180. With respect to computer-aided surgical devices 104, for example, the computing device 106 may communicate control parameters corresponding to a three-dimensional model of the resection volume as determined from Boolean operations between the pathologic bone surface and the new bone surface. More specifically, the computing device 106 may subtract the three-dimensional model of the new bone surface determined in step 208 from the three-dimensional model of the pathologic femur 306 to result in a three-dimensional model of the resection volume. The computing device 106 may also perform similar Boolean operations for each radial or axial slice of the femur 306 in the two-dimensional domain. For example, subtracting the two-dimensional image of the new contour $p_s$-$p_2$ of the femur 306 from a two-dimensional image of the pathologic femur 306 may provide a closed contour, as shown in FIG. 18. Repeating the Boolean operation for each cross-section may provide a series of closed contours which may further be stacked, as shown in FIG. 19, so as to construct the corresponding resection volume in the three-dimensional space. Although the views shown in FIGS. 18 and 19 may suggest closed contours that are formed within axial cross-sections or slices of the femur 306, the algorithm 200 may alternatively be configured to form closed contours within radial cross-sections or slices that are rotatably stackable about the neck axis NA.

Figure 20:
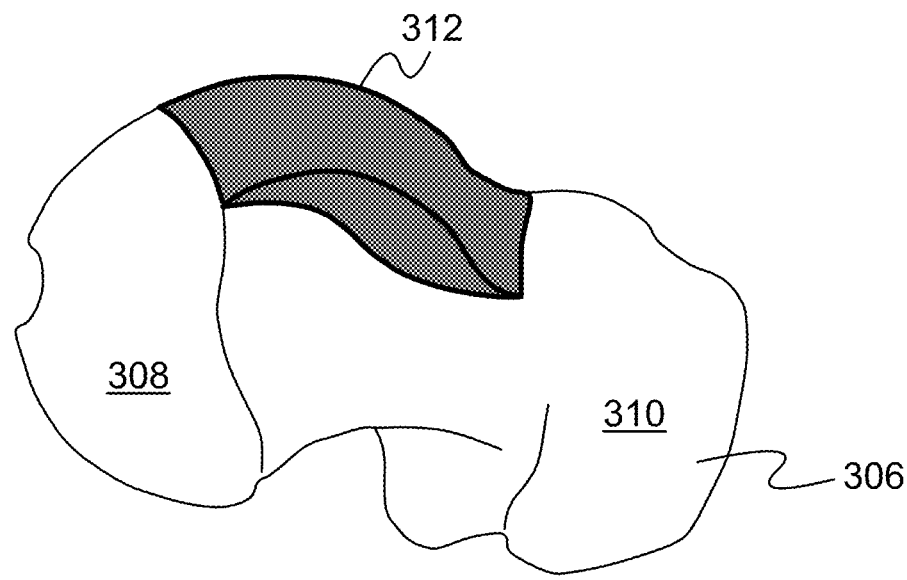
FIG. 20 is an axial view of a pathologic femur and a resection volume thereof.
Figure 21:
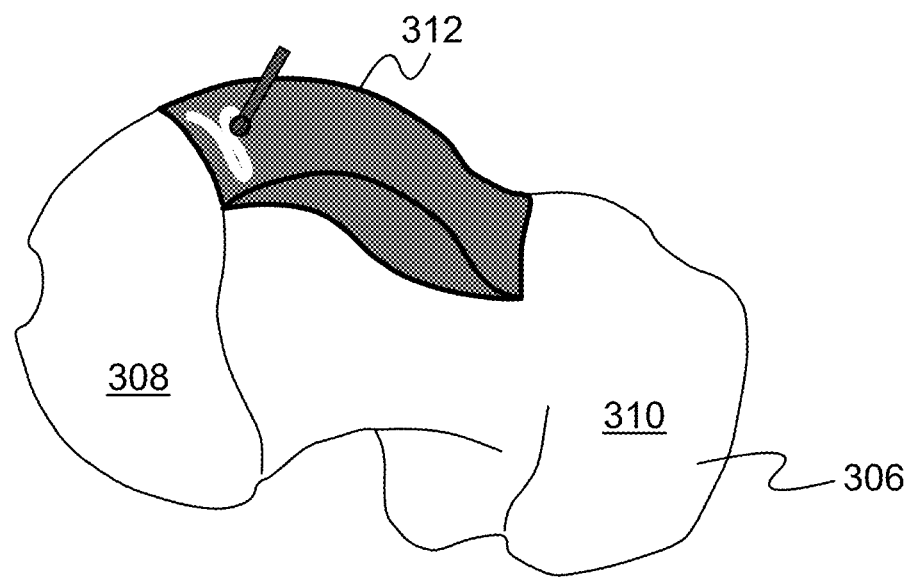
FIG. 21 is another axial view of a pathologic femur and a resection volume thereof.
Figure 22:
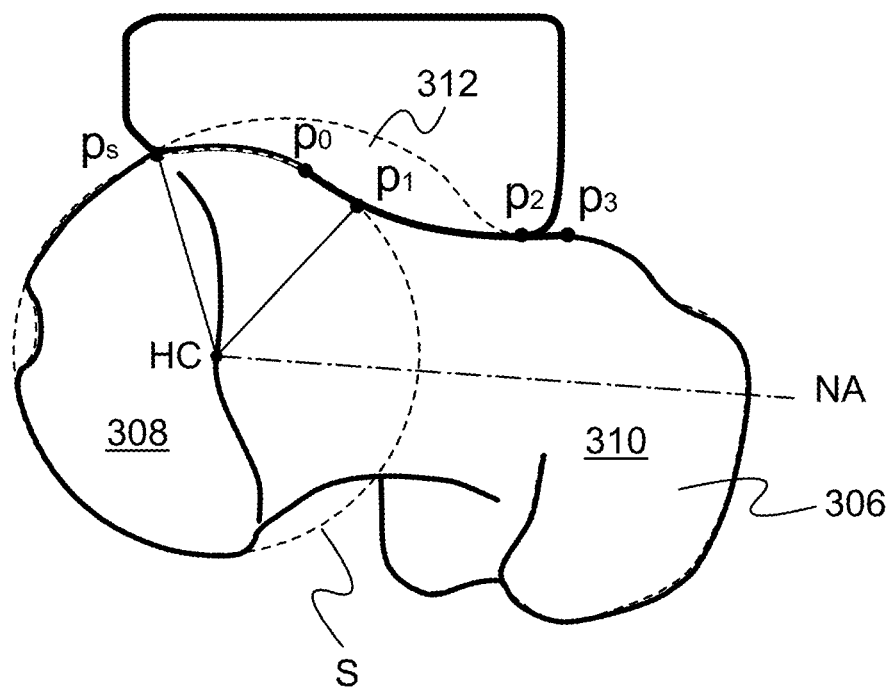
FIG. 22 is an axial cross-sectional view of a pathologic femur and a closed planar contour thereof.
Figure 23:
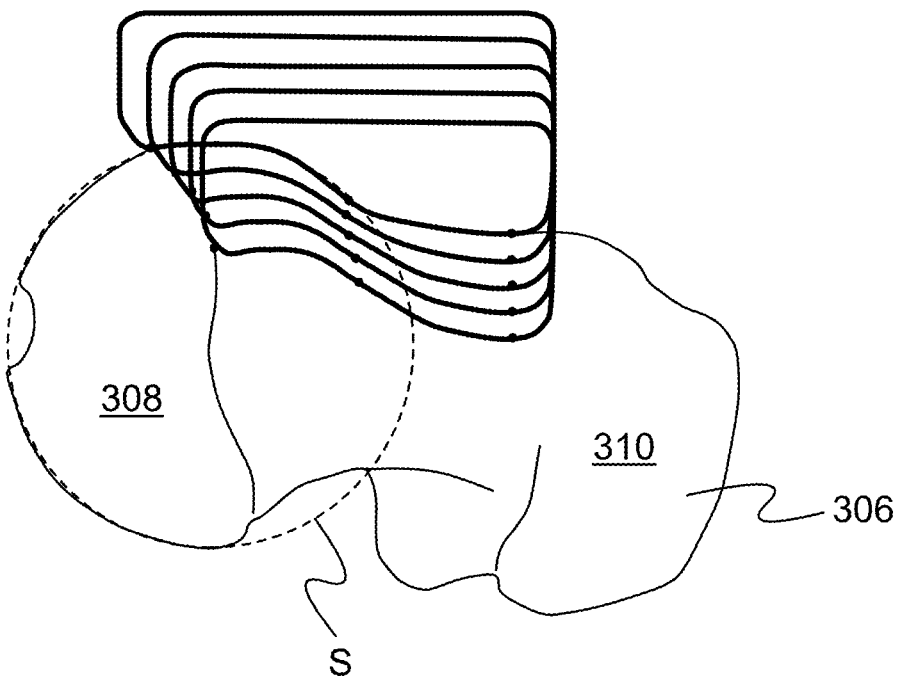
FIG. 23 is an axial view of a pathologic femur and a plurality of closed planar contours thereof.
Figure 24:
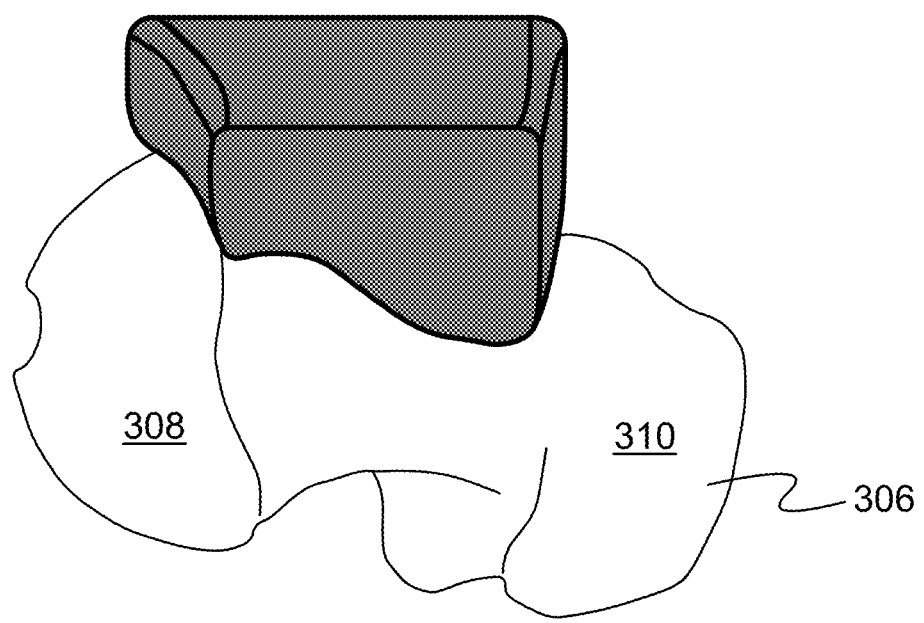
FIG. 24 is an axial view of a pathologic femur and a closed resection volume thereof.

By stacking the closed contours, the computing device 106 may be able to generate the three-dimensional model of the resection volume as shown in FIG. 20. The computing device 106 may also communicate control parameters corresponding to the resulting resection volume to the appropriate surgical device 104, for example, at a substantially high refresh rate or in real-time, so as to visually guide the user during the surgical procedure. For instance, as shown in FIG. 21, the computing device 106 may be configured to distinguish, such as by color code, the resection volume from the remainder of the femur 306. Alternatively, in haptic- or robot-guided surgical applications, the computing device 106 may communicate control parameters corresponding to a closed volume, as illustrated in FIGS. 22-24. More specifically, the computing device 106 may generate a series of planar contours using two or more curve segments, for example, the segments $p_s$-$p_0$ and $p_0$-$p_2$ of the desired resection contours of FIGS. 22 and 23. By combining the planar contours of FIG. 23, the computing device 106 may be able to construct the three-dimensional closed resection volume of FIG. 24, and further, relay control parameters corresponding to the closed resection volume to the appropriate haptic- or robot-guided surgical devices 104. In still further modifications, the computing device 106 may be adapted to construct radial rather than planar contours that are constructed using the resection contours of FIG. 12, for example, and rotatably combined about the neck axis NA to form the closed resection volume. Such closed resection volumes may further ensure that the surgical device 104 is maintained within the boundaries of the resection volume throughout the surgical procedure and that no additional bone mass is unnecessarily removed.

In still further modifications, such as in the optional step 210 of FIG. 3, the computing device 106 may be configured to enable evaluation of the range of motion of the hip joint 300 with the newly generated bone surface and/or resection volume. More specifically, the computing device 106 may simulate kinematics of the hip joint 300 using graphical models or image representations generated from steps 201-208 of FIG. 3. Such evaluations may be used to determine if the resection volume will adequately and sufficiently correct the pathologic joint 300, and if not, aid the user in determining the specific adjustments to be made. For example, if a planned resection to the hip joint 300 results in an insufficient range of motion, the evaluation step 210 may aid the user in visually and more accurately determining the particular areas of the resection volume needing adjustments. While the evaluation step 210 may be manually operated via user control, the kinematic simulations may also be automatically performed and assessed by the computing device 106. Furthermore, the evaluations of step 210 may be performed prior to communicating the control parameters of step 209 such that any revisions to the resection volume or the surgical plan may be made prior to actual implementations.

Based on the foregoing, it can be seen that the present disclosure provides a more streamlined approach for planning and performing surgical treatment of orthopedic impingement conditions. More specifically, the present disclosure provides surgical planning methods and systems which enable more conventional, more efficient and more accurate determination of the resection volume of a commonly treated anatomic structure. While only certain embodiments have been set forth for the purposes of illustration, alternatives and modifications will be apparent from the above description to those skilled in the art. These and other alternatives are considered equivalents and within the spirit and scope of this disclosure and the appended claims.

What is claimed is:

1. A method for determining a resection volume of a pathologic femur having a femoral head and a femoral neck, comprising the steps of:
   determining a first point of a desired contour based on a pathologic alpha angle of the pathologic femur;
   determining a second point of the desired contour based on a desired alpha angle of the pathologic femur;
   determining a third point of the desired contour on the femoral neck of the pathologic femur; and
   generating, at a processor, a resection volume of the pathologic femur based on a three-dimensional reconstruction of the first, second and third points of the desired contour obtained from each of a plurality of cross-sections of the pathologic femur.

2. The method of claim 1, wherein the desired contour is determined for each of a plurality of radial slices disposed about an axis of the femoral neck and between an arc of resection, the resection volume being generated by superimposing the three-dimensional reconstruction of the desired contours onto a three-dimensional model of the pathologic femur.

3. The method of claim 1, wherein the desired contour is determined for each of a plurality of axial cross-sections extending between a superior end and an inferior end of the pathologic femur, the resection volume being generated by superimposing the three-dimensional reconstruction of the desired contours onto a three-dimensional model of the pathologic femur.

4. The method of claim 1 further comprising the step of determining a fourth point of the desired contour on at least one of the femoral head and the femoral neck of the pathologic femur.

5. The method of claim 1 further comprising the step of evaluating a range of motion of the femur with the generated resection volume by simulating hip kinematics.

6. A method for determining a resection volume of a pathologic femur having a femoral head and a femoral neck, comprising the steps of:
receiving medical images of the pathologic femur from a medical imaging device;
determining landmarks of the pathologic femur based on the medical images;
determining at least a first contour point and a second contour point of the pathologic femur, the first contour point corresponding to a pathologic alpha angle, the second contour point corresponding to a desired alpha angle;
determining a morphing region on the pathologic femur; and
generating, at a processor, a resection volume based on a three-dimensional reconstruction of the first contour point, the second contour point and the morphing region obtained from each of a plurality of cross-sections of the pathologic femur.

7. The method of claim 6, wherein the second contour point corresponds to an end of a resection of a slice.

8. The method of claim 6, wherein the landmarks include a femoral head center, a femoral neck center and a femoral neck axis intersecting the femoral head center and the femoral neck center, the femoral head being derived from one of a least squares sphere fit of the femoral head, and a plurality of two-dimensional circles approximating cross-sectional perimeters of the femoral head.

9. The method of claim 8, wherein the two-dimensional circles are derived using automatic edge detection filters on the axial cross-sections of the femoral head.

10. The method of claim 6, wherein the first contour point is the point where the pathologic femoral head deviates from a sphere approximating the femoral head, and the pathologic alpha angle is the angle between an axis of the femoral neck and a line connecting a center of the femoral head with the first contour point.

11. The method of claim 6, wherein a desired contour is determined based on at least the first contour point, the second contour point and the morphing region for each of a plurality of radial slices disposed about a femoral neck axis and between an arc of resection, the resection volume being generated by superimposing the three-dimensional reconstruction of the desired contours onto a three-dimensional model of the pathologic femur.

12. The method of claim 11, wherein the arc of resection is automatically determined based on a relative depth of an overgrowth for each radial slice, the relative depth being measured at a predefined angle with the femoral neck axis.

13. The method of claim 12, wherein the arc of resection is configured to include one or more radial slices having relative depths with negative indices.

14. The method of claim 6, wherein a desired contour is determined based on at least the first contour point, the second contour point and the morphing region for each of a plurality of axial cross-sections extending between a superior end and an inferior end of the pathologic femur, the resection volume being generated by superimposing the three-dimensional reconstruction of the desired contours onto a three-dimensional model of the pathologic femur.

15. The method of claim 14, wherein the desired contours are closed planar contours.

16. The method of claim 6 further comprising the step of communicating control parameters corresponding to the resection volume to a surgical device.

17. The method of claim 6 further comprising the step of evaluating a range of motion of the femur with the generated resection volume by simulating hip kinematics.

18. A system for resectioning a pathologic femur having a femoral head and a femoral neck, comprising:
at least one medical imaging device configured to output medical images of the pathologic femur; and
a computing device in communication with the medical imaging device, the computing device including a memory and a processor configured to receive the medical images from the medical imaging device, determine a first point of a desired contour based on a pathologic alpha angle of the pathologic femur, determine a second point of the desired contour based on a desired alpha angle of the pathologic femur, determine a desired morphing region of the pathologic femur, and generate a resection volume of the pathologic femur based on a three-dimensional reconstruction of the first point, the second point and the desired morphing region obtained from each of a plurality of cross-sections of the pathologic femur.

19. The system of claim 18 further comprising at least one surgical device, the computing device being configured to communicate control parameters corresponding to the resection volume to the surgical device.

20. The system of claim 18, wherein the computing device is in communication with a display device and an input device, the display device being configured to display the medical images to a user, the input device being configured to receive input from the user corresponding to at least the desired alpha angle and the desired morphing region.

* * * * *